(12) United States Patent
Ruppin et al.

(10) Patent No.: US 8,420,864 B2
(45) Date of Patent: Apr. 16, 2013

(54) HIGH-PURITY N-ETHYLMETHYLAMINE AND PROCESS FOR PREPARING SAME

(75) Inventors: Christophe Ruppin, Saint-Pierre D'Albigny (FR); Jacqueline Dufour, Saint Michel de Maurienne (FR)

(73) Assignee: Arkema France, Colombes (FR)

( * ) Notice: Subject to any disclaimer, the term of this patent is extended or adjusted under 35 U.S.C. 154(b) by 288 days.

(21) Appl. No.: 12/996,454

(22) PCT Filed: Jul. 2, 2009

(86) PCT No.: PCT/FR2009/051281
§ 371 (c)(1),
(2), (4) Date: Jan. 7, 2011

(87) PCT Pub. No.: WO2010/001055
PCT Pub. Date: Jan. 7, 2010

(65) Prior Publication Data
US 2011/0166387 A1  Jul. 7, 2011

(30) Foreign Application Priority Data
Jul. 4, 2008  (FR) ..................................... 08 54563

(51) Int. Cl.
*C07C 209/26* (2006.01)

(52) U.S. Cl.
USPC .......................................................... 564/473

(58) Field of Classification Search .................. 564/473, 564/497, 499
See application file for complete search history.

(56) References Cited

U.S. PATENT DOCUMENTS

| 5,225,597 | A | * | 7/1993 | Kurek ........................... 564/446 |
| 5,773,658 | A | * | 6/1998 | Weber et al. .................. 564/473 |
| 6,111,141 | A | * | 8/2000 | Eller et al. .................... 564/473 |
| 6,982,352 | B2 | * | 1/2006 | Lappe et al. .................. 564/471 |

OTHER PUBLICATIONS

Database CAPLUS on STN, Acc. No. 2007:1258677, Kang, CN 101062901 A (Oct. 31, 2007) (abstract).*
International Search Report (and English Translation) received in PCT/FR2009/051281 mailed Dec. 3, 2009.

* cited by examiner

*Primary Examiner* — Brian J Davis
(74) *Attorney, Agent, or Firm* — Smith, Gambrell & Russell, LLP

(57) ABSTRACT

Disclosed herein is N-ethylmethylamine having a very high degree of purity, that is to say very low contents of impurities commonly encountered in conventional industrial processes, and a process for preparing, on an industrial scale, high-purity N-ethylmethylamine.

27 Claims, No Drawings

HIGH-PURITY N-ETHYLMETHYLAMINE AND PROCESS FOR PREPARING SAME

The present invention relates to N-ethylmethyl-amine having a very high degree of purity, that is to say very low contents of impurities customarily encountered in conventional industrial processes, and also to the process for preparing, on an industrial scale, high-purity N-ethylmethylamine.

N-Ethylmethylamine (for which the acronym "EMA" is used in the remainder of the present document) is a speciality amine of increasing use, especially as a synthesis intermediate, in various fields of application.

For example, in pharmacy, EMA is involved in the manufacture of active molecules intended for the treatment of degenerative diseases of the nervous system. A development is also observed in electronic applications, especially for the synthesis of metal salts, such as for example tetrakis(ethylmethylamino)hafnium or tetrakis(ethylmethylamino)zirconium. These metal salts are volatile precursors of choice for producing deposits of metal films in the manufacture of semiconductors.

The two fields of application set out above, and many others too, are examples which illustrate the need to be able to provide high-purity EMA on an industrial scale.

In order to obtain high-purity EMA, it could indeed be envisaged to purify EMA of technical grade, by means of one or more filtrations, distillations, crystallizations, and other means commonly used for the purification of organic compounds.

Such operations, although they can be carried out on a laboratory scale, are not entirely suitable for industrial productions, due in particular to energy costs, effluent volumes, infrastructures, etc. which would result in a high-purity EMA that is not very profitable from an economic viewpoint.

Currently, EMA can be obtained by alkylation of ethylamine with a methyl halide (for example methyl iodide). This process is however not very selective since it does not make it possible to avoid certain parasitic reactions, such as dialkylation; moreover, this process generates saline effluents that are difficult to recycle and to remove.

Other known processes for the synthesis of EMA are gas-phase catalytic processes, for example starting from ethylamine and methanol or from monomethylamine and ethanol. The harsh synthesis conditions used result however in low yields via secondary production of dimethylethylamine or diethylmethylamine.

Another possible pathway, under milder conditions, consists in forming EMA via a conventional reductive amination reaction starting from ethylamine and formol. But this synthesis route does not make it possible to obtain EMA of good purity, due to the parasitic formation of dimethylethylamine, the boiling point of which (37° C.) is very close to that of EMA (33° C.)

The dimethylethylamine by-product is therefore very difficult to separate from the EMA via conventional purification processes such as fractional distillation, and the industrial synthesis of high-purity EMA cannot therefore be envisaged by this route.

Therefore, there remains a need for a process for the synthesis of EMA that is selective, gives a high yield, generates few or no by-products, and is easy to implement from an industrial viewpoint, thus enabling access to a high-purity EMA, with production volumes and costs compatible with the requirements of the industries in question.

The Applicant has now discovered that it is possible to obtain high-purity EMA according to a selective and easily industrializable process. The degree of purity of the EMA obtained according to the invention is greater than or equal to 99%, preferably greater than 99.5% by weight.

Thus, according to a first aspect, the invention relates to a composition comprising an amount greater than or equal to 99%, preferably greater than or equal to 99.5%, more preferably greater than or equal to 99.8% by weight of N-ethylmethylamine (EMA), and an amount of N,N-dimethylethylamine (DMEA) of less than 0.1% by weight, preferably of less than 0.05% by weight, more preferably of less than 0.02% by weight, advantageously of less than 100 ppm by weight.

More particularly, the invention relates to a composition comprising:
a) an amount greater than or equal to 99%, preferably greater than or equal to 99.5%, more preferably greater than or equal to 99.8% by weight of N-ethylmethylamine (EMA);
b) from 0 to 0.05%, preferably from 0 to 0.02% by weight of dimethylamine (DMA);
c) from 0 to 0.05%, preferably from 0 to 0.02% by weight of diethylamine (DEA);
d) from 0 to 0.05% by weight, preferably from 0 to 0.02% by weight, more preferably from 0 to 100 ppm by weight of dimethylethylamine (DMEA);
e) from 0 to 0.2%, preferably from 0 to 0.1% by weight of diethylmethylamine (DEMA);
f) from 0 to 0.2%, preferably from 0 to 0.1% by weight of unreacted starting compounds, other by-products (such as, for example, trimethylamine); and
g) the balance to 100% by weight of water, preferably from 0 to 0.2%, more preferably from 0 to 0.1% by weight of water.

In one preferred embodiment, the invention relates to a composition comprising:
a) an amount greater than or equal to 99%, preferably greater than or equal to 99.5%, more preferably greater than or equal to 99.8% by weight of N-ethylmethylamine (EMA);
and one or more of the following compounds b) to f):
b) from 0.0005% (5 ppm) to 0.05%, preferably from 5 ppm to 0.02% by weight of dimethylamine (DMA);
c) from 0.0005% (5 ppm) to 0.05%, preferably from 5 ppm to 0.02% by weight of diethylamine (DEA);
d) from 0.0005% (5 ppm) to 0.05%, preferably from 0.0005% to 0.02% by weight, more preferably from 5 ppm to 100 ppm by weight of dimethylethylamine (DMEA);
e) from 0.0005% (5 ppm) to 0.2%, preferably from 5 ppm to 0.1% by weight of diethylmethylamine (DEMA);
f) from 0.0005% (5 ppm) to 0.2%, preferably from 5 ppm to 0.1% by weight of unreacted starting compounds, other by-products (such as, for example, trimethylamine); and
g) the balance to 100% by weight of water, preferably from 5 ppm to 0.2%, more preferably from 5 ppm to 0.1% by weight of water.

According to another preferred embodiment, the invention relates to a composition comprising an amount greater than or equal to 99%, preferably greater than or equal to 99.5%, more preferably greater than or equal to 99.8% by weight of N-ethylmethylamine (EMA), from 0.0005% (5 ppm) to 0.05%, preferably from 0.0005% to 0.02% by weight, more preferably from 5 ppm to 100 ppm by weight of dimethylethylamine (DMEA) and the balance to 100% by weight of water, preferably from 5 ppm to 0.2%, more preferably from 5 ppm to 0.1% by weight of water.

According to another preferred embodiment, the invention relates to a composition comprising:
a) an amount greater than or equal to 99%, preferably greater than or equal to 99.5%, more preferably greater than or equal to 99.8% by weight of N-ethylmethylamine (EMA);

b) from 0.0005% (5 ppm) to 0.05%, preferably from 5 ppm to 0.02% by weight of dimethylamine (DMA);
c) from 0.0005% (5 ppm) to 0.05%, preferably from 5 ppm to 0.02% by weight of diethylamine (DEA);
d) from 0.0005% (5 ppm) to 0.05%, preferably from 0.0005% to 0.02% by weight, more preferably from 5 ppm to 100 ppm by weight of dimethylethylamine (DMEA);
e) from 0.0005% (5 ppm) to 0.2%, preferably from 5 ppm to 0.1% by weight of diethylmethylamine (DEMA);
f) from 0.0005% (5 ppm) to 0.2%, preferably from 5 ppm to 0.1% by weight of unreacted starting compounds, other by-products (such as, for example, trimethylamine); and
g) the balance to 100% by weight of water, preferably from 5 ppm to 0.2%, more preferably from 5 ppm to 0.1% by weight of water.

According to another preferred embodiment, the invention relates to a composition comprising:
a) an amount greater than or equal to 99.5%, more preferably greater than or equal to 99.8% by weight of N-ethylmethylamine (EMA);
b) from 0.0005% (5 ppm) to 0.02%, preferably from 5 ppm to 0.01% by weight of dimethylamine (DMA);
c) from 0.0005% (5 ppm) to 0.02%, preferably from 5 ppm to 0.01% by weight of diethylamine (DEA);
d) from 0.0005% (5 ppm) to 0.02%, preferably from 5 ppm to 100 ppm by weight of dimethylethylamine (DMEA);
e) from 0.0005% (5 ppm) to 0.2%, preferably from 5 ppm to 0.1% by weight of diethylmethylamine (DEMA);
f) from 0.0005% (5 ppm) to 0.2%, preferably from 5 ppm to 0.1% by weight of unreacted starting compounds, other by-products (such as, for example, trimethylamine); and
g) the balance to 100% by weight of water, preferably from 5 ppm to 0.1%, more preferably from 5 ppm to 0.05% by weight of water.

The N-ethylmethylamine of the invention, with the degrees of purity and optional impurities defined above (that is to say the compositions defined above) is obtained by a selective process for the reductive amination of acetaldehyde by monomethylamine.

Thus, according to another aspect, the present invention relates to a process for preparing high-purity EMA, and in particular the compositions defined previously, comprising an amount greater than or equal to 99%, preferably greater than 99.5% by weight of EMA, which process is characterized by particular conditions for implementing the reaction steps, that make it possible to improve the selectivity and the yield of the synthesis.

More precisely, the process of the invention is characterized by the fact that it comprises at least the following steps:
a) preparation of a mixture comprising mono-methylamine, at least one hydrogenation catalyst and a catalytic amount of at least one strong base;
b) stirring of the mixture and heating to a reaction temperature between 20° C. and 120° C., preferably between 50° C. and 80° C., more preferably between 60° C. and 75° C., under hydrogen pressure;
c) addition of acetaldehyde to the mixture kept at temperature and under pressure of hydrogen;
d) recovery of the reaction medium after separation of the catalyst; and
e) purification of the EMA, preferably by fractional distillation, in order to obtain the high-purity EMA according to the invention.

According to one preferred embodiment, the process of the invention is a semi-continuous process, but adapting it to a continuous process is easy to carry out and is within the capabilities of a person skilled in the art.

The starting monomethylamine (MMA) can be used as is (gaseous under normal temperature and pressure conditions, sold under the name "anhydrous" MMA), or in the form of an aqueous solution. However, it is preferred to use it in the form of an aqueous solution, for example at a dilution between 10% and 90% by weight of MMA relative to the total weight of the solution, preferably between 20% and 60% by weight, in particular around 40% by weight.

When the reaction is carried out starting from anhydrous MMA, this is used in the liquid state under pressure and the reaction is generally carried out without any solvent. When the reaction is carried out in the liquid phase, the preferred solvent is water (in which the monomethylamine is solubilized). However, it is possible to use other solvents, the nature of which may be very variable, as long as the solvent is inert with respect to the reaction in question and miscible with water. Examples of solvents are, non-limitingly, alcohols, especially ethanol, isopropanol, etc.

The hydrogenation catalyst that may be used in the process of the invention is of any type known to a person skilled in the art specialized in the field of the hydrogenation of organic compounds. It is preferred to use any type of catalyst customarily used for catalytic hydrogenation reactions in a heterogeneous medium.

Non-limiting examples of such catalysts may be chosen from hydrogenation catalysts based on metals from Groups 8, 9, 10 and 11 of the Periodic Table of the Elements (IUPAC), preferably Raney catalysts based on Ni, Co or Cu and also Pd (Pd/C type) and more particularly Raney nickel catalysts. Similarly, the amount of catalyst will be chosen depending on the type of catalyst, the reaction conditions, etc., as a person skilled in the art knows. As a general rule, the amount of catalyst used is such that the catalyst concentration relative to the anhydrous MMA is between 0.1 and 50% by weight, preferably between 1% and 25% and more particularly between 5% and 20%.

Added to the monomethylamine and to the catalyst is a catalytic amount of at least one strong base. The expression "catalytic amount" is understood to mean an amount of strong base between 0.15 mol % and 4 mol %, preferably between 0.4 mol % and 2 mol % and more particularly between 0.75 mol % and 1.5 mol % relative to the anhydrous MMA.

The strong base may be any type of mineral or organic strong base. Moreover, water-soluble bases are preferred. Mineral bases are also preferred, among these alkali and/or alkaline-earth metal hydroxides, more precisely potassium and/or sodium hydroxides.

The use of sodium and/or potassium hydroxide enabled a very selective process to be carried out with good yields and enabled EMA of very high purity to be obtained.

The mixture is stirred, under hydrogen pressure, and brought to a temperature between 20° C. and 120° C., preferably between 40° C. and 100° C., more particularly between 50° C. and 80° C., typically between 60° C. and 75° C.

At the predefined temperature, the pressure is adjusted by addition of hydrogen, so that the pressure in the reactor is between atmospheric pressure and 15 MPa, preferably between 0.5 MPa and 8 MPa, and more particularly between 1 and 5 MPa.

Acetaldehyde (AcH) is added to the reaction medium over a period which may vary between 30 minutes and 10 hours, preferably between 2 hours and 5 hours, while keeping the pressure constant, by adding hydrogen as it is consumed. The amount of acetaldehyde added is such that the MMA/AcH molar ratio is between around 0.5 and around 1.25, preferably between 0.75 and 1.0 and more particularly between 0.85 and 0.95.

The reaction time may vary considerably depending on the amount of reactants used, the reaction temperature, the hydrogen pressure, but as a general rule the reductive amination reaction is carried out for a period between 30 minutes and 10 hours, preferably between 2 hours and 5 hours.

The reaction is considered to be complete when it is no longer necessary to add hydrogen to the reactor in order to keep the pressure constant, at a given temperature.

At the end of the reaction, the catalyst is removed by any means known to a person skilled in the art, for example by sedimentation, filtration, etc., sedimentation being preferred. After removing the catalyst, the liquid is involved in a purification step, preferably subjected to a fractional distillation, preferably at atmospheric pressure, in order to recover the high-purity N-ethylmethylamine according to the invention.

The catalyst can thus be used again for a series of numerous cycles for the synthesis of high-purity EMA (for example from 2 to a few tens, typically from 10 to 100 cycles), by recharging the reactor with the MMA, the strong base, the hydrogen and the AcH, as indicated above.

The distillation is preferably carried out under atmospheric pressure, but it would not be outside the scope of the invention to operate under pressure, or under vacuum.

Moreover, the distillation is advantageously carried out with a side stream, typically at the level of the upper quarter of the column, ideally at a level between 75% and 95% of the height of the column.

Furthermore, and if necessary as a function of the applications, the water content may be further reduced by increasing the reflux ratio used during the distillation and/or by any complementary water-extraction treatment known to a person skilled in the art, such as drying over molecular sieves or by membrane pervaporation.

The present invention is now illustrated by means of the examples which follow, which have no limiting character, and which cannot consequently be understood as capable of restricting the scope of the invention as claimed.

EXAMPLE 1

According to the Invention

Introduce successively into a 250 l hydrogenation autoclave equipped with a stirring system and a heating/cooling system are 89.5 kg of monomethylamine (commercial 40.5 wt % aqueous solution, i.e. 36.2 kg of anhydrous MMA), around 5.5 kg of Raney nickel (weight concentration of nickel in the catalyst greater than 82%) and around 0.65 kg of sodium hydroxide that is introduced in the form of an aqueous solution with a titre of 450 g/l.

The whole assembly is placed under hydrogen pressure and heated at a temperature of around 65-67° C. Acetaldehyde (56.3 kg) is then introduced into the autoclave over a period of around 3.3 hours. The hydrogen pressure is maintained at around 3 MPa, over the duration of the reaction. After adding all of the acetaldehyde, the reaction is maintained at temperature and under hydrogen pressure until the consumption of hydrogen stops (i.e. around 1 hour).

At the end of the reaction, the N-ethylmethyl-amine selectivity, with respect to the acetaldehyde, is 85.6 mol %, and the molar yield of EMA is 93% relative to the starting monomethylamine.

The stirring is stopped, the autoclave is degassed and the catalyst is left to settle. The supernatant liquid is then withdrawn and subjected to a fractional distillation under atmospheric pressure in a column comprising around 15 to 20 theoretical plates. After removing the light fractions, the high-purity EMA is recovered via a side stream at a column height of around 90%, with a distillation yield (degree of recovery of EMA relative to the EMA in the crude reaction medium) of 95%.

The composition of organic constituents of the high-purity EMA is determined quantitatively and qualitatively by gas chromatography (with internal calibration). The concentration of residual water in the EMA is assayed by potentiometric titration according to the Karl-Fischer method.

Thus, an EMA having a purity of 99.86% by weight is obtained, the composition of which is presented in the table below:

| Nature of the constituent | Amount by weight (%) |
|---|---|
| EMA | 99.87 |
| MMA | 0.008 |
| DMA | 0.011 |
| Trimethylamine | 0.007 |
| DMEA | 0.010 |
| DEA | 0.004 |
| DEMA | 0.050 |
| Undefined | 0.010 |
| Water | 0.030 |

EXAMPLE 2

Comparative

The reaction for the synthesis of EMA is carried out according to Example 1 above, with an amount of sodium hydroxide of only 0.05 mol % relative to the anhydrous MMA introduced.

The N-ethylmethylamine is obtained in the crude reaction medium with a selectivity, with respect to the acetaldehyde, of only 67.6 mol %, due to the formation of a large amount of DEMA (17.2% selectivity with respect to acetaldehyde), and of heavy compounds (13% selectivity with respect to acetaldehyde).

The invention claimed is:

1. A process for preparing a composition comprising N-ethylmethylamine (EMA) in an amount greater than or equal to 99% by weight, and N,N-dimethylethylamine (DMEA) in an amount less than 0.1% by weight, which comprises at least the following steps:
   a) preparing a mixture comprising monomethylamine, at least one hydrogenation catalyst, and a catalytic amount of at least one strong base;
   b) stirring the mixture and heating to a reaction temperature between 20° C. and 120° C. under hydrogen pressure;
   c) adding acetaldehyde to the mixture kept at temperature and under pressure of hydrogen;
   d) recovering the reaction medium after separation of the catalyst; and
   e) purifying the high-purity EMA.

2. The process according to claim 1, wherein the process is a semi-continuous process.

3. The process according to claim 1, wherein the monomethylamine is introduced in the form of an aqueous solution at a dilution between 10% and 90% by weight of MMA relative to the total weight of the aqueous solution.

4. The process according to claim 1, wherein the catalyst is selected from the group consisting of hydrogenation catalysts based on metals from Groups 8, 9, 10 and 11 of the Periodic Table of the Elements.

5. The process according to claim 1, wherein the strong base is added to the reaction medium in an amount between 0.15 mol % and 4 mol % relative to the anhydrous MMA.

6. The process according to claim 5, wherein the strong base is sodium hydroxide.

7. The process according to claim 1, wherein the monomethylamine/acetaldehyde molar ratio is between about 0.5 and about 1.25.

8. The process according to claim 1, wherein after removal of the catalyst, the reaction medium is purified by fractional distillation.

9. The process according to claim 8, wherein the fractional distillation is carried out with a side stream.

10. The process according to claim 1, wherein the mixture is heated to a reaction temperature in the range of about 50° C. to about 80° C. under hydrogen pressure.

11. The process according to claim 1, wherein the mixture is heated to a reaction temperature in the range of about 60° C. to about 75° C. under hydrogen pressure.

12. The process according to claim 1, wherein the monomethylamine is introduced in the form of an aqueous solution, at a dilution between 20% and 60% by weight of MMA relative to the total weight of the aqueous solution.

13. The process according to claim 1, wherein the monomethylamine is introduced in the form of an aqueous solution at a dilution 40% by weight of MMA relative to the total weight of the aqueous solution.

14. The process according to claim 1, wherein the at least one hydrogenation catalyst is a Raney catalyst based on Ni, Co, or Cu, and palladium (Pd/C).

15. The process according to claim 1, wherein the at least one hydrogenation catalyst is a Raney nickel catalyst.

16. The process according to claim 1, wherein the strong base is added to the reaction medium in an amount between 0.4 mol % and 2 mol % relative to the anhydrous MMA.

17. The process according to claim 1, wherein the strong base is added to the reaction medium in an amount between 0.75 mol % and 1.5 mol % relative to the anhydrous MMA.

18. The process according to claim 1, wherein the monomethylamine/acetaldehyde molar ratio is between 0.75 and 1.0.

19. The process according to claim 1, wherein the monomethylamine/acetaldehyde molar ratio is between 0.85 and 0.95.

20. The process according to claim 8, wherein the fractional distillation is performed at atmospheric pressure.

21. The process according to claim 8, wherein the distillation is carried out with a side stream at a level between 75% and 95% of the height of the column.

22. The process according to claim 9, wherein the fractional distillation is carried out at the level of the upper quarter of a distillation column.

23. The process according to claim 1, wherein the composition comprises greater than or equal to 99.5% by weight of N-ethylmethylamine (EMA).

24. The process according to claim 1, wherein the composition comprises greater than or equal to 99.8% by weight of N-ethylmethylamine (EMA).

25. The process according to claim 1, wherein the composition comprises less than 0.05% by weight of N,N-dimethylethylamine (DMEA).

26. The process according to claim 1, wherein the composition comprises less than 100 ppm by weight of N,N-dimethylethylamine (DMEA).

27. The process according to claim 1, wherein the composition further comprises dimethylamine (DMA), diethylamine (DEA), diethylmethylamine (DEMA), unreacted starting compounds, water, or one or more combinations thereof.

* * * * *